US012788853B2

(12) United States Patent
Claassen et al.

(10) Patent No.: US 12,788,853 B2
(45) Date of Patent: Nov. 10, 2026

(54) BREAST PUMP

(71) Applicant: KONINKLIJKE PHILIPS N.V., Eindhoven (NL)

(72) Inventors: Coen Petrus Martinus Claassen, Lommel (BE); Gijsbert Hendrik Van Veldhuizen, Groningen (NL); Lili-Marjan Brockhuis, Geldrop (NL); Adrianus Wilhelmus Dionisius Maria Van Den Bijgaart, Helvoirt (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 723 days.

(21) Appl. No.: 18/036,682

(22) PCT Filed: Nov. 12, 2021

(86) PCT No.: PCT/EP2021/081484

§ 371 (c)(1),
(2) Date: May 12, 2023

(87) PCT Pub. No.: WO2022/101391

PCT Pub. Date: May 19, 2022

(65) Prior Publication Data

US 2023/0338630 A1 Oct. 26, 2023

(30) Foreign Application Priority Data

Nov. 16, 2020 (EP) .................................... 20207695

(51) Int. Cl.
*A61M 1/06* (2006.01)

(52) U.S. Cl.
CPC ............ *A61M 1/066* (2014.02); *A61M 1/067* (2021.05); *A61M 2205/587* (2013.01); *A61M 2209/088* (2013.01)

(58) Field of Classification Search
CPC ...... A61M 1/06; A61M 1/069; A61M 1/0693; A61M 1/0697; A61M 1/066; A61M 1/067;

(Continued)

(56) References Cited

U.S. PATENT DOCUMENTS 9,033,913 B2 5/2015 Khalil
2008/0275386 A1 11/2008 Myers (Continued)

FOREIGN PATENT DOCUMENTS

CN 210228764 U 4/2020
WO 200029044 A2 5/2000

(Continued)

OTHER PUBLICATIONS

International Search Report and Written Opinion of PCT/EP2021/081484, dated Feb. 16, 2022.

*Primary Examiner* — Jason E Flick

(57) ABSTRACT

A breast pump comprises an outer housing for mounting over the breast and an inner breast shield which is transparent at least in the region of the nipple. The outer housing has a window in an upper portion of the outer housing, for enabling, in use, a direct line of sight for the user of the breast pump, through the window to the nipple. The remainder of the outer housing blocks a view of the nipple from at least directly in front.

18 Claims, 4 Drawing Sheets

(58) Field of Classification Search
CPC ...... A61M 2205/587; A61M 2209/088; A61M 2205/585; A61M 2205/583; A61M 1/064; A61M 1/062; A61J 13/00
See application file for complete search history.

(56) References Cited

U.S. PATENT DOCUMENTS

| | | | | |
|---|---|---|---|---|
| 2011/0245763 | A1* | 10/2011 | Myers | A61M 1/064 604/74 |
| 2015/0141761 | A1 | 5/2015 | O'Malley | |
| 2016/0008526 | A1 | 1/2016 | Tatterfield | |
| 2020/0139026 | A1 | 5/2020 | O'Toole | |
| 2023/0117214 | A1* | 4/2023 | Makower | A61M 1/064 604/74 |

FOREIGN PATENT DOCUMENTS

| | | | | |
|---|---|---|---|---|
| WO | WO-0029044 | A2 * | 5/2000 | A61B 5/444 |
| WO | 2016014469 | A1 | 1/2016 | |
| WO | 2020046777 | A1 | 3/2020 | |

* cited by examiner

BREAST PUMP

CROSS-REFERENCE TO PRIOR APPLICATIONS

This application is the U.S. National Phase application under 35 U.S.C. § 371 of International Application No. PCT/EP2021/081484, filed on Nov. 12, 2021, which claims the benefit of European Patent Application No 20207695.6, filed on Nov. 16, 2020. These applications are hereby incorporated by reference herein.

FIELD OF THE INVENTION

This invention relates to breast pumps.

BACKGROUND OF THE INVENTION

Breast pumps are used by breast feeding women to extract milk such that the extracted milk can be fed to their babies at a later time.

Typically, the breast is placed into a funnel shaped cup and a vacuum is applied such that milk is extracted. The breast pump typically has two operating modes, namely a stimulation mode and an extraction mode. During the stimulation mode, the milk ejection reflex is stimulated. When the breast pump is activated, a pressure source such as a vacuum pump inside the breast pump generates a vacuum and the stimulation mode can be started. The vacuum pump is typically driven by an electric motor. For portable breast pumps, these motors are driven by battery power.

Wearable breast pumps are characterized in that they can be fully worn on the user's body, allowing the user to move around freely. Some of these are small enough to fit into a user's bra. A motor, battery and milk container are for example integrated to form a single unit.

Nipple alignment is key to comfort and effectiveness of a breast pump. If the nipple is not well aligned, there can be uncomfortable or painful friction between the nipple and breast pump, or the openings of the milk ducts at the tip of the nipple can be blocked.

Being able to see the nipple while positioning the funnel shaped cup is therefore key. For this reason it is known to provide a transparent nipple shield, which is first positioned over the breast, before the remainder of the breast pump. This means there are multiple steps required when preparing to express milk, and this may be inconvenient, for example especially when in a public environment.

WO 2020/046777 discloses a breast pump system which includes an outer shell including a cut out feature at the front that provides a visual path to an interior of the breast pump. In this way, a user can ensure that nipple alignment is achieved or maintained when the pump is in its fully assembled and pumping configuration. However, it is difficult to see the nipple using the front cut out feature, for example a mirror is proposed inside the cap to improve visibility. In addition, a front cut out feature enables other people to see the interior of the breast pump and the positioned nipple from the front, which may be indiscrete or experienced as obtrusive.

US 2016/008526 discloses a breast pump and relates to a design of a liner which prevents the user from needing to adopt a leaning forward posture. The liner is transparent so that there is a view of the nipple for monitoring purposes during operation.

SUMMARY OF THE INVENTION

The invention is defined by the claims.

According to examples in accordance with an aspect of the invention, there is provided a breast pump, comprising:

an outer housing for mounting over the breast;

a breast shield received in the outer housing, comprising a transparent nipple-receiving portion at the end of a breast-receiving portion;

a pump;

a connection interface for connection to a milk container; and a controller for implementing a cyclic pressure waveform to the breast shield, wherein the outer housing has a window in an upper portion of the outer housing, for enabling, in use, a direct line of sight for the user of the breast pump, through the window to the nipple-receiving portion of the breast shield, and wherein the outer housing blocks a view of the nipple-receiving portion from at least directly in front to prevent visibility to third parties.

In this design, a direct view is provided for the user of the breast pump of the nipple-receiving portion of the breast shield so that correct alignment can be assessed. However, this view is provided discretely by blocking this view from in front. Thus, only user is able to make a visual inspection.

The components along the line of sight to the nipple of the user include primarily the window and the nipple portion of the breast shield. Any other components, such as a membrane, are also transparent. This means a least obstructed view is provided of the nipple area of the breast pump. All components along this line of sight are thus transparent, and the few components there are, the less obstructed the view will be.

A view of the nipple-receiving portion is preferably blocked for a range of view directions including from directly in front and a cone formed by an angle of at least 10 degrees all around the view from directly in front (the apex of the cone being at the nipple-receiving portion, and the cone volume defining an volume from which a line of sight is blocked).

The view of the nipple-receiving portion may be blocked for a cone formed by an angle of at least 20 degrees, for example an angle of at least 30 degrees, for example an angle of at least 40 degrees, all around the view from directly in front.

In this way, the view is blocked for different height people at different distances and different lateral angles from the user.

The breast pump preferably further comprises the milk container. The breast shield is preferably removably received in the outer housing. The whole of the breast shield may be a single molded transparent component, but only the nipple-receiving portion needs to be transparent for the purposes of implementing the invention.

The window for example comprises an opening in the outer housing.

In one example, a removable cover is provided over the opening. In another example, a fixed transparent cover is provided over the opening.

In another example, there is a lens within or over the opening.

The outer housing and breast shield are preferably coupled together for fitting to the breast as a single unit. The alignment of the breast shield over the breast may thus be performed with the breast pump fully assembled. This reduces the number of steps in fitting the breast pump.

It is of course also possible to apply the breast shield first, and then apply the outer housing over the breast shield (in more conventional manner).

The milk container is for example attachable to a base of the outer housing, and the pump is within the outer housing. Thus, the milk container and the outer housing connect to form a single unit.

An illumination source may be provided for illuminating a space inside the nipple-receiving portion. This assists the viewing of the nipple to set the correct alignment.

The breast pump is preferably a wearable breast pump, for example arranged to be supported by a breast feeding bra.

The controller controls the vacuum applied to the breast shield, i.e. the internal space of the breast shield, to provide a cyclic waveform with different vacuum levels applied over time. For example, the controller may be adapted to implement at least two operating modes comprising a stimulation mode and an extraction mode, with different cyclic frequency and different maximum under-pressure levels.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
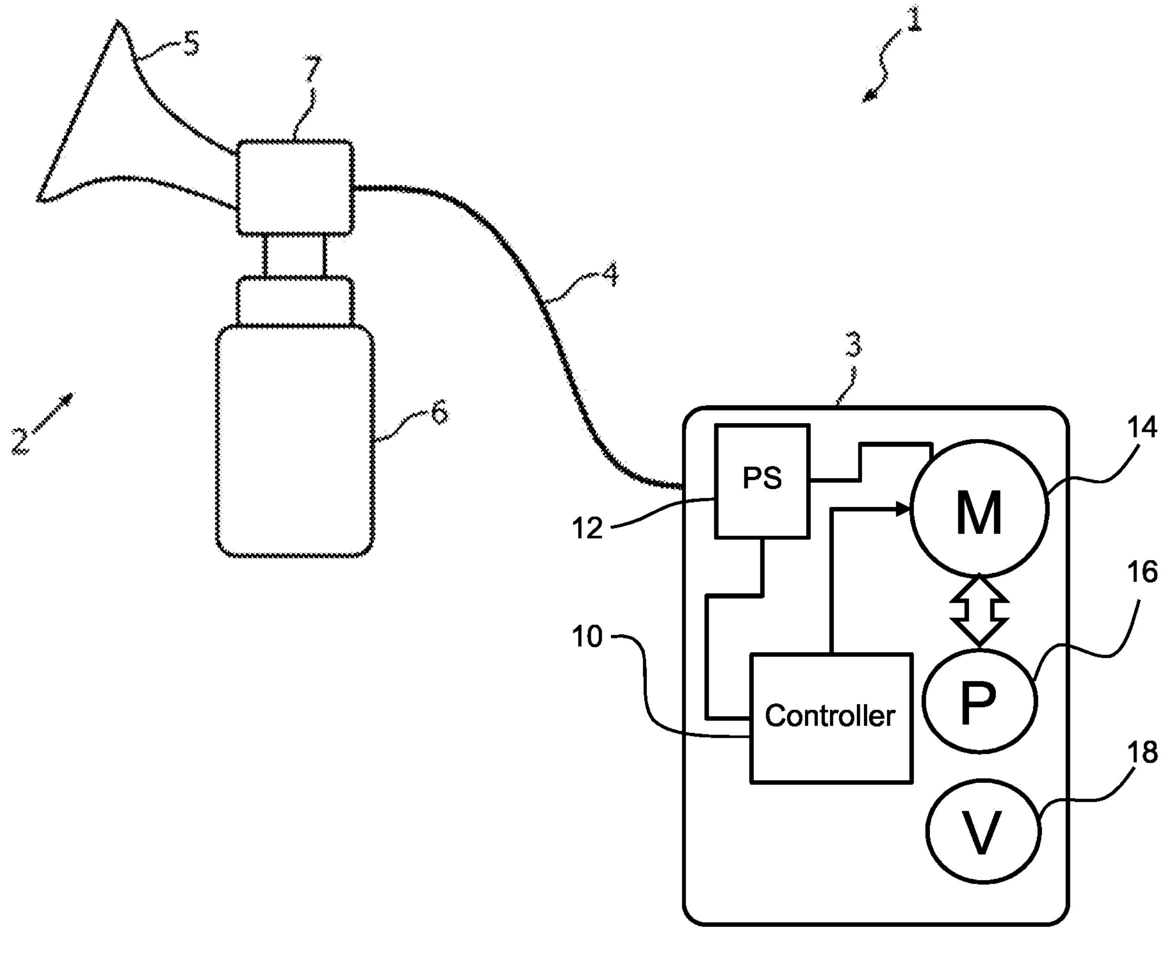
FIG. 1 PRIOR ART
FIG. 1 shows a known breast pump system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a breast pump which comprises an outer housing for mounting over the breast and an inner breast shield which is transparent at least in the region of the nipple. The outer housing has a window in an upper portion of the outer housing, for enabling, in use, a direct line of sight for the user of the breast pump, through the window to the nipple. The remainder of the outer housing blocks a view of the nipple from in front.

FIG. 1 shows a known breast pump system 1, comprising an expression unit 2 and a pump arrangement 3 which are connected via a tube 4. The pump arrangement includes various components in addition to the pump, so may be considered to be a general operating unit.

The expression unit 2 is formed with a main body 7, a funnel 5 for receiving a breast of a user and a receptacle 6 for collecting the expressed milk. The funnel 5 and the receptacle 6 are connected to the main body 7. The main body 7 comprises a vacuum chamber. A flexible membrane or diaphragm is located in the vacuum chamber. The membrane prevents expressed milk from flowing into the tube 4 leading to the pump arrangement unit 3.

The pump arrangement 3 may instead be directly mounted and connected to the main body 7. In this case, the membrane prevents expressed milk from flowing directly into the pump arrangement 3.

The pump arrangement 3 comprises a controller 10, a power source 12, a motor 14 and a vacuum pump 16. The controller controls 10 the operation of the power source 12, motor 14 and vacuum pump 16. The pump arrangement 3 further comprises a solenoid valve 18.

In use, the vacuum pump applies a vacuum to the membrane located in the main body 7 so that it deforms. The membrane deforms to create a vacuum in the funnel 5 which in turns applies a vacuum to the breast which enables milk to be expressed. Although the breast pump system 1 is described as comprising a membrane such that the vacuum is applied indirectly to the breast, it should be understood that in an alternative embodiment, the vacuum is applied directly to the breast of a user. In this case, the breast pump system does not comprise a membrane and the vacuum created by the vacuum pump is applied directly to the breast.

The vacuum is applied to the breast at intervals. That is, a pressure differential is applied on a cyclic basis. After a vacuum has been established, the pressure from the vacuum is released by the use of the solenoid valve which is temporarily opened. The solenoid valve is an electromechanically operated valve configured to open and close an air passage that connects to the vacuum side of the vacuum pump to ambient air such that when the solenoid valve is closed, the vacuum pump generates a vacuum in the expression unit which enables milk to be expressed from the breast of a user. When the solenoid valve is opened, the vacuum generated by the vacuum pump is released as ambient air flows towards the vacuum or negative pressure created by the vacuum pump such that the pressure exerted on the breast of a user is partially or completely reduced.

This is a basic description of the known operation of a standard breast pump system.

There are also wearable breast pumps, which are for example for mounting within a feeding bra. All of the drivetrain components described above are then formed within an outer enclosure which fits over the breast. A top part contains the drivetrain (pump, motor, controller) and a bottom part forms the collection vessel. This enables breast pumping to be performed more discretely.

Figure 2:
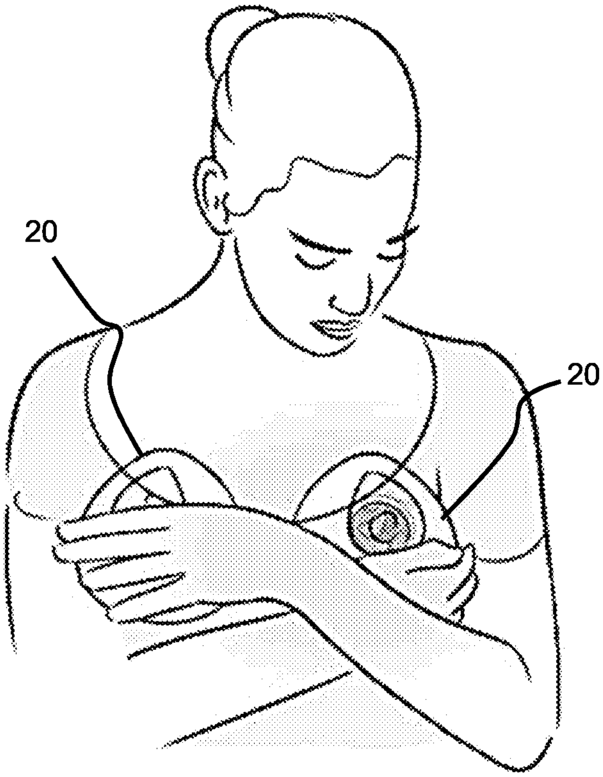
FIG. 2 PRIOR ART
FIG. 2 shows a mother wearing two wearable breast pumps.

FIG. 2 shows a mother wearing two wearable breast pumps 20.

In such a design, the funnel 5 of FIG. 1 is implemented as breast shield, and this breast shield is received within an outer enclosure of the wearable breast pump.

The invention relates to the positioning of the breast shield over the breast. Correct alignment is crucial to a successful expression session. For this purpose, it is known to provide a transparent breast shield so that alignment can be visually inspected.

Figure 3:
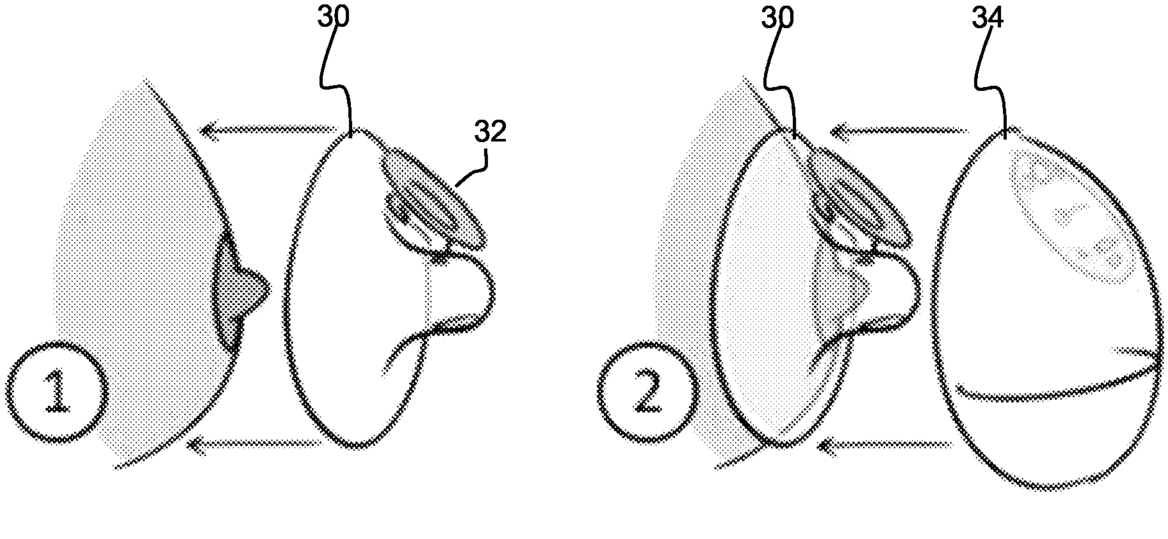
FIG. 3 PRIOR ART
FIG. 3 shows the positioning of a known wearable breast pump.

As shown in FIG. 3, the positioning of a known wearable breast pump involves first fitting the breast shield 30 over the breast. The breast shield 30 has a port 32 for receiving vacuum pressure from the drivetrain of the breast pump. The outer enclosure 34 is then mounted over the fitted breast shield 30. It makes a connection to the port 32 so that the desired pressure profile may be applied to the breast.

The invention relates generally to a breast pump in which there is a separate breast shield and an outer housing within which the breast shield is received. The invention is of particular interest for wearable breast pumps, but it may be applied to other types of breast pump, for example wearable expression kits with remote pump system.

A wearable expression kit may for example be worn in a bra. This expression kit may then be connected to separate vacuum source, for example a breast pump device in the user's pocket. The milk container and breast interface would remain in the wearable bra form factor, but other components such as, but not limited to the motor, air valve, battery, and user interface could be located outside the bra and worn or carried somewhere else on the body. This would allow a more compact form factor.

Figure 4:
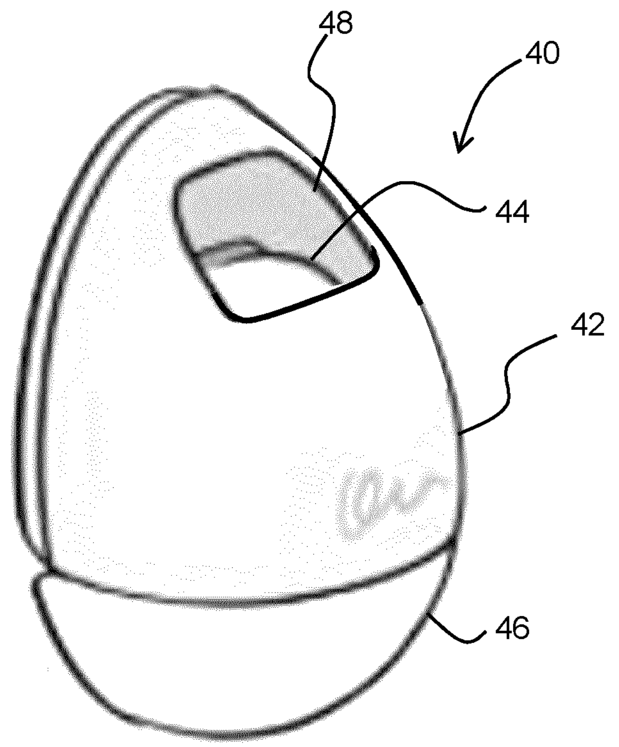
FIG. 4 shows a breast pump in accordance with the invention.

FIG. 4 shows a breast pump 40 in accordance with the invention. In this example, all parts are integrated as a single unit for mounting in a breast feeding bra. The breast pump comprises an outer housing 42 for mounting over the breast and a transparent breast shield 44 removably received in the outer housing 42. The breast shield 44 comprises a nipple-receiving portion at the end of a breast-receiving portion.

The outer enclosure 42 houses a motor, pump, battery, and controller, i.e. electronics. The controller controls a cyclic pressure waveform applied to the breast shield (to be applied directly to the breast or via a separate membrane). These components are all standard and thus will not be described in detail.

A milk container 46 is removably attachable to a base part of the housing 42.

The outer housing 42 has a window 48 in an upper portion of the outer housing. The window enables, in use, a direct line of sight for the user of the breast pump to the nipple portion of the breast shield 44. However, the remainder of the outer housing blocks a view of the nipple-receiving portion from in front.

Thus, a direct view is provided of the nipple-receiving portion of the breast shield so that correct alignment can be assessed. Because the view is blocked from in front, only the user is able to make a visual inspection, making the design more discrete.

The only components along the line of sight to the nipple of the user are the window and the nipple portion of the breast shield 44. This means a least obstructed view is provided of the nipple area of the breast pump.

The window 48 is shown as an opening in the outer housing. A removable opaque cover may be provided over the opening or else a fixed transparent cover may be provided over the opening. The transparent cover (fixed or removable) may comprise a lens that improves the visibility of the nipple and nipple alignment (by enlarging or shrinking the visual image). The transparent cover may also have visual alignment features to assist the user in making the correct alignment.

The opening may even be permanently open, but it is preferred for aesthetic reasons as well as for protection of the components inside the breast pump for the opening to be covered.

When a cover is used, it preferably forms a smooth continuous surface with the remainder of the housing so that there is no step in or out from the housing to the cover. The cover thus has a shape which blends with the natural shape of the housing.

Figure 5:
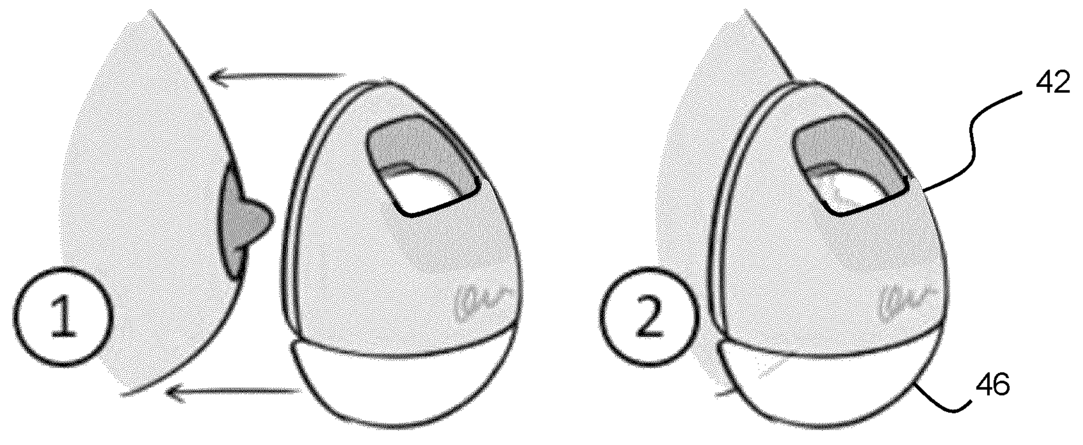
FIG. 5 shows how the outer housing and breast shield couple together for fitting to the breast as a single unit.

FIG. 5 shows how the outer housing and breast shield couple together for fitting to the breast as a single unit. The alignment of the breast shield over the breast may thus be performed with the breast pump fully assembled. This reduces the number of steps in fitting the breast pump.

Figure 6:
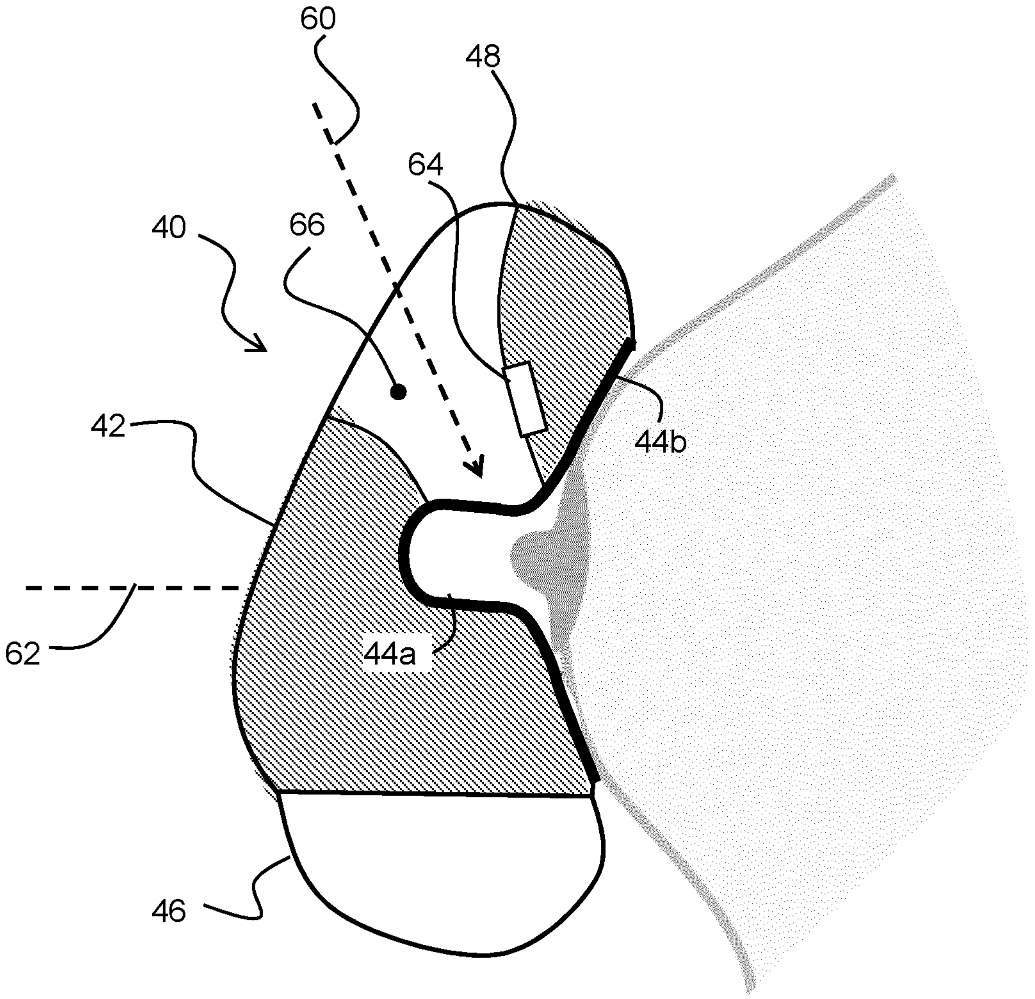
FIG. 6 shows in schematic form the optical paths.

FIG. 6 shows in schematic form the optical paths, including the line of sight 60 to the nipple-receiving portion 44*a* of the breast shield 44 and the blocked forward path 62. It also shows the breast-receiving portion 44*b* of the breast shield 44.

The blocked forward path 62 is the path directly forward from the breast pump, i.e. horizontal when the breast pump is in a normal worn position and the wearer is standing upright. The nipple receiving portion may be blocked for a range of view directions, such as the direct path and a cone formed by an angle of at least 10 degrees all around the direct path, or at least 20 degrees, or at least 30 degrees or at least 40 degrees.

Thus, the viewing directions for a typical range of heights of third parties and lateral positions relative to the user are blocked.

An optional illumination source 64 is also shown illuminating a space inside the nipple-receiving portion 44*a*. This assists the viewing of the nipple to set the correct alignment.

The drivetrain components of the breast pump are positioned around the recess 66 defined beneath the window 48. Any parts along the line of sight 60 are transparent including the breast shield. As mentioned above, the breast pump may have a membrane as well as the breast shield, the membrane surrounding the nipple and fitted into a membrane chamber. The membrane and the breast shield are then transparent to allow visibility of the nipple.

The window is of sufficient size to provide a line of sight for the expected body geometry of a typical range of users. It for example has a lower edge above the nipple and preferably a distance, e.g. at least 10 mm, above the nipple so that even from eye level in front of the user, the nipple-receiving portion is not visible. As shown in FIG. 6, from in front, only surfaces of the enclosure walls, e.g. those that define the recess 66, may be visible.

The invention is applied to cyclic pumping breast pump devices as described above. Such devices have a controller for controlling the vacuum applied to the internal space of the breast shield, so that the vacuum has a cyclic waveform with different vacuum levels applied over time. The controller may be provided within the housing, or it may be part of a remote pump unit when there is a separate expression kit and pump unit, as explained above. The controller may alter the drive signal to the pump motor, or it may control a pressure regulator, or both.

The breast pump for example has two operating modes implemented by the controller, namely a stimulation mode and an extraction mode. These modes for example have different cyclic frequency and different maximum under-pressure (i.e. vacuum) levels.

The expression mode for example cycles between a baseline vacuum and a maximum vacuum (i.e. a maximum under-pressure) "Max_Vac".

There is first a time to (maximum) vacuum, TTV, then a dwell-in time DI, then a time to atmosphere (or to the baseline vacuum), TTA, and finally a dwell-out time, DO. The vacuum rate is defined as Max_Vac/TTV and the atmospheric rate is defined as Max_Vac/TTA.

By way of example:
Baseline_Vac=atmospheric pressure
Max_Vac=300 mbar (30 kPa) below atmospheric pressure $$TTV = 0.85\ \mathrm{s}$$

$$DI = 0.3\ \mathrm{s}$$

$$TTA = 0.05\ \mathrm{s}$$

$$DO = 0.35\ \mathrm{s}$$

This gives a total cycle time T_cycle of 1.55s.

These values are simply by way of example. The maximum under-pressure may be higher, for example 350 mbar (35 kPa) and the durations may differ. The cycle time is generally of the order of 1 to 2 seconds.

The stimulation mode has a faster frequency hence with a shorter cycle time of around 0.5 seconds, and a lower vacuum, for example a maximum under-pressure level of 150 mbar (15 kPa). The stimulation mode for example takes placing during an initial period of the breast pumping session (e.g. 50 seconds) and the expression mode takes place during the remainder of the breast pumping session.

The controller may also implement a positioning mode. This may comprise intermittent application of a small under-pressure to allow the user to position the breast shield while observing the correct alignment.

The controller may also implement a massage mode.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. A breast pump comprising:
an outer housing for mounting over a breast;
a breast shield received in the outer housing, comprising a transparent nipple-receiving portion at an end of a breast-receiving portion; and
a controller for implementing a cyclic pressure waveform to the breast shield,
wherein the outer housing has a window in an upper portion of the outer housing, for enabling, in use, a direct line of sight for a user of the breast pump, through the window to the nipple-receiving portion of the breast shield, and wherein the outer housing blocks a view of the nipple-receiving portion from at least directly in front of the nipple-receiving portion to prevent visibility to third parties.

2. The breast pump of claim 1, wherein a view of the nipple-receiving portion is blocked for a range of view directions including from directly in front of the nipple-receiving portion and a cone formed by an angle of at least 10 degrees all around the view from directly in front of the nipple-receiving portion.

3. The breast pump of claim 2, wherein a view of the nipple-receiving portion is blocked for a range of view directions including from directly in front of the nipple-receiving portion and a cone formed by an angle of at least 20 degrees all around the view from directly in front of the nipple-receiving portion.

4. The breast pump of claim 1, wherein the breast shield is removably received in the outer housing.

5. The breast pump of claim 1, wherein components along a line of sight to a nipple of the user include the window and the nipple-receiving portion of the breast shield.

6. The breast pump of claim 1, wherein the window comprises an opening in the outer housing.

7. The breast pump of claim 1, wherein the outer housing and breast shield are coupled together for fitting to the breast as a single unit.

8. The breast pump of claim 1, comprising an illumination source for illuminating a space inside the nipple-receiving portion.

9. The breast pump of claim 1, wherein the breast pump is configured to be worn by the user.

10. The breast pump of claim 1, wherein the controller is adapted to implement at least two operating modes comprising a stimulation mode and an extraction mode, with different cyclic frequency and different maximum under-pressure levels.

11. The breast pump of claim 1, further comprising a milk container.

12. The breast pump of claim 11, wherein the milk container is attachable to a base of the outer housing, and a pump is within the outer housing.

13. The breast pump of claim 1, wherein the breast pump:
is a wearable breast pump for mounting within a feeding bra, or
comprises a wearable expression kit, the wearable expression kit comprising a milk container and the breast shield, wherein the milk container and the breast shield are to be worn in a bra.

14. The breast pump of claim 1, wherein the window enables, in use, the direct line of sight for the user of the breast pump to the nipple-receiving portion of the breast shield and a remainder of the outer housing blocks the view of the nipple-receiving portion from in front.

15. The breast pump of claim 1, wherein all components along the line of sight are transparent.

16. The breast pump of claim 1, wherein components along the line of sight to the nipple of the user are limited to the window and the nipple-receiving portion of the breast shield.

17. The breast pump of claim 1, further comprising:
a membrane for preventing expressed milk from flowing into a pump.

18. A wearable expression kit for use with a pump, the pump to be located outside a user's bra during use of the wearable expression kit and to be worn or carried somewhere else on the user, the wearable expression kit comprising:
an outer housing for mounting over a breast;
a breast shield received in the outer housing, comprising a transparent nipple-receiving portion at an end of a breast-receiving portion; and
a milk container;
wherein the outer housing has a window in an upper portion of the outer housing, for enabling, in use, a direct line of sight for a user of the wearable expression kit, through the window to the nipple-receiving portion of the breast shield, and wherein the outer housing is adapted, in use with the user standing upright, to block a view of the nipple-receiving portion from at least horizontally and laterally directly in front of the nipple-receiving portion to prevent visibility to third parties, wherein the milk container and the breast shield are to be worn in a bra.

* * * * *